(12) United States Patent
Deininger

(10) Patent No.: US 10,347,480 B2
(45) Date of Patent: Jul. 9, 2019

(54) METHOD FOR EVALUATING THE QUALITY OF MASS SPECTROMETRIC IMAGING PREPARATIONS AND KIT-OF-PARTS THEREFOR

(71) Applicant: Bruker Daltonik, GmbH, Bremen (DE)

(72) Inventor: Sören-Oliver Deininger, Leipzig (DE)

( * ) Notice: Subject to any disclaimer, the term of this patent is extended or adjusted under 35 U.S.C. 154(b) by 0 days.

(21) Appl. No.: 15/714,269

(22) Filed: Sep. 25, 2017

(65) Prior Publication Data

US 2019/0096650 A1 Mar. 28, 2019

(51) Int. Cl.
| | |
|---|---|
| *H01J 49/16* | (2006.01) |
| *H01J 49/00* | (2006.01) |
| *B01D 59/44* | (2006.01) |
| *H01J 49/04* | (2006.01) |
| *G01N 27/64* | (2006.01) |
| *G01N 33/68* | (2006.01) |
| *H01J 49/40* | (2006.01) |

(52) U.S. Cl.
CPC ............ *H01J 49/164* (2013.01); *B01D 59/44* (2013.01); *G01N 27/64* (2013.01); *G01N 33/6851* (2013.01); *H01J 49/0004* (2013.01); *H01J 49/0418* (2013.01); *H01J 49/40* (2013.01)

(58) Field of Classification Search
CPC .... H01J 49/164; H01J 49/0004; H01J 49/168; H01J 49/0418; H01J 49/40; B01D 59/44; G01N 27/64; G01N 33/6851
See application file for complete search history.

(56) References Cited

U.S. PATENT DOCUMENTS

| | | | | |
|---|---|---|---|---|
| 5,808,300 | A * | 9/1998 | Caprioli | H01J 49/0004 250/281 |
| 5,910,656 | A * | 6/1999 | Koster | H01J 49/0409 250/252.1 |
| 8,012,693 | B2 * | 9/2011 | Chong Conklin | G01N 1/30 435/23 |
| 2009/0325222 | A1 * | 12/2009 | Agar | G01N 1/30 435/40.5 |
| 2015/0118694 | A1 * | 4/2015 | Andersson | G01N 33/557 435/7.23 |

FOREIGN PATENT DOCUMENTS

| | | |
|---|---|---|
| EP | 2388797 A1 | 11/2011 |
| EP | 2455759 A1 | 5/2012 |

OTHER PUBLICATIONS

Erich et al, "Scores for Standardization of On-Tissue Digestion of Formalin-Fixed Paraffin-Embedded Tissue in MALDI-MS Imaging", Biochim. Biophys. Acta 2016.*
Oetjen et al, "An Approach to Optimize Sample Preparations for MALDI Imaging MS of FFPE Sections Using Fractional Factorial Design of Experiments", Anal. Bioanal. Chem. 2016 408:6729-40.*

(Continued)

*Primary Examiner* — David E Smith
(74) *Attorney, Agent, or Firm* — Benoit & Côté Inc.

(57) ABSTRACT

The invention relates to a method for evaluating a quality of preparations of analytical tissue sections for mass spectrometric imaging using a reference sample to be processed and measured alongside the analytical tissue sections, and a kit-of-parts for a mass spectrometric imaging experiment including such reference sample.

20 Claims, 8 Drawing Sheets

(56) References Cited

OTHER PUBLICATIONS

Erich et al, "Scores for Standardization of On-Tissue Digestion of Formalin-Fixed Paraffin-Embedded Tissue in MALDI-MS imaging", Boichim. Biophys. Acta 2016 (Year: 2016).*

Oetjen et al, "An Approach to Optimize Sample Preparation for MALDI Imaging MS of FFPE Sections Using Fractional Factorial Design of Experiments", Anal. Bioanal. Chem. 2016 408:6729-40 (Year: 2016).*

Groseclose, M. R., "A Mimetic Tissue Model for the Quantification of Drug Distributions by MALDI Imaging Mass Spectrometry", Analytical Chemistry, 2013. dx.doi.org/10.1021/ac400892z.

Cazares, L.H. et al., "Imaging Mass Spectrometry of a Specific Fragment of Mitogen-Activated Protein Kinase/Extracellular Signal-Regulated Knase Knase Knase 2 Discriminates Cancer from Uninvolved Prostate Tissue", Clinical Cancer Research, vol. 15, No. 17, Sep. 1, 2009.

Alice, Ly, et al., "High-mass-resolution MALDI mass spectrometry imaging of metabolites from formalin-fixed paraffin-embedded tissue", Nature Protocols, Nature Publishing Group, GB, vol. 11, No. 8, Aug. 1, 2016.

* cited by examiner

METHOD FOR EVALUATING THE QUALITY OF MASS SPECTROMETRIC IMAGING PREPARATIONS AND KIT-OF-PARTS THEREFOR

BACKGROUND OF THE INVENTION

Field of the Invention

The invention relates to the virtually objective evaluation of the quality of mass spectrometric imaging preparations, in particular formalin-fixed, paraffin-embedded (FFPE) tissues and further particularly using the matrix-assisted laser desorption/ionization (MALDI) technique for the mass spectrometric measurement.

Description of the Related Art

Mass spectrometric imaging of tissue using the MALDI technique has been pioneered by Richard M. Caprioli, then at the University of Texas in Houston. FIGS. 1 and 2 are adapted from his disclosure U.S. Pat. No. 5,808,300 which is incorporated herein by reference in its entirety. FIG. 1 shows a typical experimental procedure, in flow diagram form, for the image analysis of a tissue from an animal. The experimental protocol is stated to potentially involve normal metabolic events, drug therapy, tumour growth, etc. FIG. 2 schematically represents an overall imaging process likewise depicted as a flow diagram. The exemplary tissue contains two areas, designated as A and P, which contain unique molecules of interest, molecules A and P, respectively. The aim of the method has been, and still is, to localize the distribution of these molecules or any other detectable molecules of interest in the tissue where a tissue can be understood to be an ensemble of similar cells from the same origin that together carry out a specific function.

In more detail, FIG. 1 generally depicts an exemplary sequence for obtaining an image analysis of biological tissue by MALDI mass spectrometry. The experimental protocol is depicted for a rat, which is sacrificed and used to generate a tissue section. The tissue section is washed, dried and then mounted on a target plate. Electrospraying or other suitable techniques may be used to apply a suitable energy-absorbing matrix onto the tissue section followed by drying. The tissue section with the dried matrix is then subjected to the image analysis process wherein a laser beam strikes the tissue section to release molecules of interest.

In further more detail, FIG. 2 depicts the sample plate with the tissue section thereon and conceptually illustrates a laser beam for striking the tissue sample at different locations when the plate moves relative to the beam. A sample is then rastered to different positions as shown and will thus generate mass spectra for mappings of the molecules A and P over the tissue section. These mass spectral data may be transferred to a computer and combined to mass spectra provided with the peaks of the molecules A and P. A total ion image may then be depicted, or alternatively a selected ion image of the molecule A or a selected ion image of the molecule P depicted.

So far, a lot of studies have shown the great potential of MALDI imaging in clinical research and a potential future use for assisting in diagnosis. However, MALDI imaging, especially in the analysis of FFPE sections, is considered a complicated technique that requires many steps in the sample preparation. For an optimal use of MALDI imaging, especially when planning a diagnostic workflow, it is necessary to optimize the conditions of the workflow and every single step for the preparation and processing of the sample in respect of robustness and quality. Although it is possible to analyse endogenous metabolites and glycans directly from FFPE-tissue [A. Ly et al., High-mass-resolution MALDI mass spectrometry imaging of metabolites from formalin-fixed paraffin-embedded tissue, Nat Protoc (2016) 11(8):1428-43; and T. W. Powers et al., Matrix assisted laser desorption ionization imaging mass spectrometry workflow for spatial profiling analysis of N-linked glycan expression in tissues, Anal. Chem. (2013) 85(20):9799-806], the most common approach is to do a spatially resolved tryptic digest of the tissue [R. Casadonte et al., Proteomic analysis of formalin-fixed paraffin-embedded tissue by MALDI imaging mass spectrometry, Nat Protoc (2011) 6(11):1695-709]. This digest step is necessary because the FFPE crosslinks proteins of interest as a result of which they cannot be measured directly.

Usually the digest is preceded by antigen retrieval ("de-crosslinking") in order to facilitate the access for the enzyme, see for example the procedures described in U.S. Pat. No. 8,012,693 B2 which is incorporated herein by reference in its entirety. The sample preparation of the FFPE section therefore usually has the following order of steps: antigen retrieval, application of Trypsin, digestion in a humid environment, application of MALDI-matrix. Each of these steps is associated with different parameters that may affect the result. Some of the goals in the sample preparation are also contradictory. The main goal is to obtain the best possible spectral quality while maintaining the best possible spatial resolution, but in practice, optimizing one parameter means to compromise on the other. Better mass spectra and thus better quality can be obtained usually by increasing the wetness of both the tryptic digest conditions as well as the matrix application step, but this comes at the price of increased spatial analyte delocalization (also called analyte blurring, redistribution, or migration).

A lot of the technologically-driven research in MALDI imaging has the aim to improve the spatial resolution such that it reaches its instrument-defined minimum, namely the spot size of the desorbing laser beam, or, using complete ablation and sub-incremental stepping, goes even beyond that [J. C. Jurchen et al.: MALDI-MS Imaging of Features Smaller than the Size of the Laser Beam, J Am Soc Mass Spectrom 2005, 16, 1654-1659]. For optimizing the sample preparation for a given biological or medical application, it is typically tried to achieve an acceptable trade-off: The biology would determine the minimum spatial resolution needed, such as by the dimension of the anatomical structures in the tissue to be investigated; then the attempt would be made to keep this spatial resolution while maximizing the spectral quality using certain measures during sample preparation and processing.

So far, to the best of the inventor's knowledge, only two studies have been published on systematic optimization of FFPE tissue sample preparation conditions and scoring of the results [K. Erich et al., Scores for standardization of on-tissue digestion of formalin-fixed paraffin-embedded tissue in MALDI-MS imaging, Biochim. Biophys. Acta (2016) doi:10.1016/j.bbapap.2016.08.020; and J. Oetjen et al., An approach to optimize sample preparation for MALDI imaging MS of FFPE sections using fractional factorial design of experiments, Anal Bioanal Chem (2016) 408:6729-40]. However, these approaches have been implemented applying different quality criteria which cannot easily be compared.

Moreover, Bernhard Spengler and co-workers have reported examples of visualizing analyte signal overlap in adjacent pixels of tissue samples using a red-green-blue (RGB) colour scheme [A. Rompp et al.: Histology by Mass Spectrometry: Label-Free Tissue Characterization Obtained from High-Accuracy Bioanalytical Imaging, Angew. Chem. Int. Ed. 2010, 49, 3834-3838; and S. Guenther et al.: AP-MALDI imaging of neuropeptides in mouse pituitary gland with 5 μm spatial resolution and high mass accuracy, International Journal of Mass Spectrometry 305 (2011) 228-237].

In view of the foregoing, there is still a need for a more universal, at least semi-quantitative way of evaluating the quality of imaging sample preparations in the field of mass spectrometry, and in particular one that accounts for migration effects in the sample itself.

SUMMARY OF THE INVENTION

The disclosure relates most generally to a method for evaluating a quality of preparations of an analytical tissue section for mass spectrometric imaging. Its most basic principle consists in providing a reference sample of known configuration which, together with an analytical tissue section or a plurality of such analytical tissue sections to be actually investigated, is subjected to joint sample preparation and processing. In so doing, any effects on analyte distribution in the samples arising from the preparation and processing can be identified in the reference sample, if it exceeds instrumental limitations, and then the analytical tissue section(s) and their images can be tagged accordingly. Mass spectrometric imaging most commonly encompasses the rastering of a two-dimensional tissue section wherein a desorbing beam, such as a laser beam for MALDI imaging, an electrospray jet/cone for desorption electrospray ionization (DESI) imaging, or a beam of primary ions for secondary ion mass spectrometry (SIMS) imaging, for example, is gradually passed over the sample. The grid points or pixels of the raster can have a dimension of the desorbing beam, such as between 1 and 50 micrometers, or can be larger than that, such as between 10 and 100 micrometers, if the desorbing beam scans a larger surface of the tissue for each acquisition to accumulate a sum ion signal therefrom, thereby enhancing sensitivity.

A sample support suitable for mass spectrometric imaging is provided. Depending on the type of mass spectrometric analyser used, such sample support can be a conductive plate, such as a stainless steel plate or a glass plate coated with a conductive layer like indium-titanium-oxide (ITO), or a plain glass plate. The sample support may have two separate, discernible regions of which one is foreseen to receive, and is preferably already loaded with, the reference sample whereas the other is intended to accommodate the actual analytical tissue section (or more than one analytical tissue section) to be investigated, such as human tissue sections from biopsies, animal organ sections and the like.

The analytical tissue section and the reference sample are deposited (preferably next to each other) on the sample support. The reference sample comprises tissue which has adjacent regions of a first type and a second type of biological material, the first type of biological material being characterized by a first mass signal profile, such as including a single characteristic mass signal or a group of characteristic mass signals (sometimes called mass signal signature). A preferred reference sample comprises a colon coil section with its series of adjacent and alternating tissue types or a testis section with its insular tubuli dispersed on a "background" of characteristic interstitial tissue. Both colon coil and testis can be taken from rodents, such as rats and mice, for instance. The dimensions of anatomical features of rat or mice testis, for instance, range from 10 to 200 micrometers and offer consequently a large host of structures well suited for the evaluation of analyte redistribution processes in tissue sections. Further alternative reference samples could comprise one or more of animal epididymis, ovary sections, spleen sections, skin sections, blood vessels and spine sections. It is also possible to use tissue surrogates composed from cultured cells that are spun (or otherwise compressed) into pellets. Using different types of cultured cells, which may have distinct and easily discernible mass signal profiles, can be used to obtain tailor-made layered pellets with alternating cell types, such as comprising clear-cut edges, line-type features and the like.

The analytical tissue section and the reference sample are jointly prepared for analysis, which includes exposure of the analytical tissue section and the reference sample to wet chemistry. It is possible to use chemically fixed samples embedded in an organic solid material, such as formalin-fixed, paraffin-embedded samples, as the analytical tissue section and the reference sample. A joint preparation can include subjecting the chemically fixed samples embedded in an organic solid material to antigen retrieval in order to facilitate decrosslinking therein. In various embodiments, the antigen retrieval may be followed by an enzymatic digest, such as a tryptic digest or glycan digest, which substantially preserves the spatial distribution. Some digests such as glycan digests may however also be carried out without prior antigen retrieval. The requirement to treat chemically fixed samples, such as FFPE samples, prior to the mass spectrometric investigation, in particular in the field of proteomics to render access to the rather large and heavy proteins, often leads to pronounced analyte delocalization (or analyte blurring, redistribution, migration) in the tissue sample due to the frequent and/or lengthy exposure to wet chemicals. The present disclosure proposes for the first time to empirically determine a scoring of the investigated analytical tissue sections on the basis of these processes that regularly manifest themselves in degraded mass spectrometric image sharpness by probing them in a reference sample as proxy. An important feature is that the reference sample shows behaviour similar to the analytical tissue sections during wet treatment and thus facilitates comparability.

Additionally or alternatively, the joint preparation can include applying a layer of matrix substance for matrix-assisted laser desorption/ionization (MALDI), such as α-cyano-4-hydroxycinnamic acid, 2,5-dihydroxybenzoic acid, or sinapinic acid, onto the analytical tissue section and the reference sample. Since a matrix substance is applied to a sample usually in liquid phase before the crystallization sets in, almost all MALDI imaging samples show pronounced analyte delocalization. The present disclosure overcomes the shortcomings of previous quality reports for mass spectrometric imaging, which are based almost exclusively on instrumental limitations or artificial/synthetic non-tissue samples, in that the effects of sample preparation and/or processing which involve wet chemistry on the sample are duly considered, and wherein the reference sample is moreover a tissue section just like any actual analytical tissue section to be investigated in mass spectrometric imaging.

Spatially resolved mass spectra are acquired from the analytical tissue section and the reference sample in a same measurement run which, as described before, may encompass rastering and probing the available tissue surface of the samples with a desorbing beam in order to generate ions from the different distinct grid points or pixels of the raster. The raster may be a regular array of grid points or pixels arranged in parallel columns and rows for both the reference sample and the analytical tissue section. Alternatively, the raster for scanning at least the reference sample may be set-up irregularly such that the borderlines between different cell types, identified for example with the aid of a highly resolved optical image, do not intersect with any pixel or grid point in order to exclude the presence of pixels containing mixed mass signal profiles before any wet treatment.

The first mass signal profile is intensity-tracked over the spatially resolved mass spectra, and an analyte delocalization feature is deduced from the intensity track(s). In some embodiments, the intensity-tracking may be limited to a single trace across the reference sample. However, in most applications, and particularly for the sake of automating the procedure, the intensity-tracking may lead to a substantial if not complete intensity-mapping of the first mass signal profile over the whole area of the reference sample. In some variants, parallel traces of like configuration in the intensity-map of the first mass signal profile may be summed up before further evaluation to yield a sum trace having better signal-to-noise properties.

In various embodiments, a second mass signal profile characteristic for the second type of biological material may be intensity-tracked over the spatially resolved mass spectra, and, using the different intensity tracks (of the first and second mass signal profiles), acquisitions can be found among the spatially resolved mass spectra from the reference sample that belong to either the first type or the second type of biological material by their first and second mass signal profiles, respectively, to define corresponding distinct areas on the reference sample, and those acquisitions can be found which are characterized by a mixture of the first and second mass signal profiles to define overlap areas on the reference sample. Distinct areas are those where the local analyte composition does not change upon processing and treatment, whereas overlap areas (if any) can be defined as those where the analyte composition changes at this pixel.

The deducing can comprise counting the number of mass spectra in the distinct areas and that in the overlap areas and forming a ratio thereof as the analyte delocalization feature. This is a simple approach which has proven to be effective and requires only a minimum of human intervention so that it is particularly fit for being automated. This approach presupposes a virtually constant area ratio of the first and second types of biological material in the reference sample which makes testis sections with their insular tubuli on a rather homogeneous background tissue a preferred choice.

In an alternative embodiment, the intensity track(s) of the first mass signal profile may cross a thin and elongate structure in the reference sample, and deducing the analyte delocalization feature can comprise using a fitting algorithm which may optionally include an analytical curve and account for a finite width of the thin and elongate structure. This structure can be an anatomical structure, such as a muscular layer which can be present in colon walls having a width of about 100 to 150 micrometers in mice and rats, for example. A likewise suitable anatomical structure could be a basal lamina layer of about 10 micrometer thickness in the appropriate reference tissue, such as testis. The analytical curve can be a Gaussian bell curve. Characteristics of the analytical curve, such as full width at half maximum (FWHM) of the Gaussian bell curve or related width measures, can serve as the analyte delocalization feature representing the spreading out of the analyte of interest that may have occurred during sample preparation and processing under wet chemistry, such as when applying a liquid matrix substance for MALDI or a liquid enzyme to effect digestion of large proteins in the tissue.

Mass spectrometric imaging can sometimes show a pronounced "edge-effect" around the edges of the tissue. This effect stems from the fact that the tissue and the underlying support can behave very differently. Even if just a small amount of analyte is delocalized off the edge of the tissue, this may result in a detectable signal in the off-tissue region. The analysis can therefore be confounded by measurements from non-tissue regions. To address this, it is possible to mask-out non-tissue acquisitions of the spatially resolved mass spectra from the intensity-tracking and deducing steps. Non-tissue mass spectra will be characterized normally by the absence of biomolecular mass signals and the presence of background ions, such as matrix (cluster) ions when using the MALDI technique, for example. This procedure could be necessary for colon coil samples while it is generally not required for testis samples due to the dense packing of the tubuli over the interstitial background in the latter. The non-tissue acquisitions for the masking-out can be identified, for example, by using an optical image of the reference sample and matching it to the spatially resolved mass spectra. As the number of non-tissue acquisitions may vary from sample to sample and as these analytically "empty" acquisitions do not contribute anything meaningful to the analysis, the method can be made more reliable by ignoring these empty sections on the sample support.

A mass spectrometric image produced from the spatially resolved mass spectra of the analytical tissue section is tagged using the analyte delocalization feature. It is particularly preferred to establish and expand a database that contains a plurality of images from investigated analytical tissue sections and the associated analyte delocalization features in order to facilitate comparison between the latter (over extensive periods of time). The database can be further subdivided into sub-databases which are grouped and later queried according to predefined criteria, such as mode of deducing the analyte delocalization feature, tissue used as the reference sample, matrix substance in case of ionization using the MALDI technique, parameters observed during wet chemistry sample preparation and processing (e.g. level of humidity; exposure time to humid conditions), and so on.

A further aspect of the present disclosure pertains to a kit-of-parts for a mass spectrometric imaging experiment, comprising a mass spectrometric sample support having a surface which is divided into a first area assigned to receiving a reference sample being configured for determining an analyte delocalization feature and a second area assigned to receiving an analytical tissue section, wherein the first area carries a reference tissue which has adjacent regions of a first type and a second type of biological material, the first type of biological material being characterized by a first mass signal profile.

The disclosure furthermore relates to a method for optimizing sample preparation conditions for mass spectrometric imaging of a tissue section. A plurality of like reference samples is provided, the reference samples comprising tissue which has adjacent regions of a first type and a second type of biological material, the first type of biological material being characterized by a first mass signal profile. A plurality of different preparation conditions is established for the plurality of reference samples, which conditions include exposure of a reference sample to wet chemistry. Each of the plurality of reference samples is prepared for analysis in accordance with one set of preparation conditions from the plurality of different preparation conditions. Spatially resolved mass spectra are acquired from the plurality of reference samples. The first mass signal profile is intensity-tracked over the spatially resolved mass spectra of each of the plurality of reference samples, and a degree of analyte delocalization is deduced from the intensity tracks in each of the plurality of reference samples. An optimal preparation condition is derived from the plurality of different preparation conditions as that which causes least delocalization in the plurality of reference samples.

This procedure provides for an expedient way of optimizing sample preparation and processing in view of the analytical question to be answered for a particular mass spectrometric imaging measurement. Due to the reproducibility of the methods presented herein, the results for particular reference tissue types and tissue conditions can be taken as valid for a large host of like measurements. In so doing, the procedure allows drawing generalized conclusions which dispenses with the need to carry out optimization procedures for each individual sample to be investigated, often a lengthy task.

It goes without saying that specific embodiments and refinements disclosed earlier in conjunction with other aspects of the present disclosure are likewise applicable to the kit-of-parts as well as the optimization procedure.

BRIEF DESCRIPTION OF THE DRAWINGS

The invention can be better understood by referring to the following figures. The elements in the figures are not necessarily to scale, emphasis instead being placed upon illustrating the principles of the invention (often schematically).

DETAILED DESCRIPTION

Figure 1:
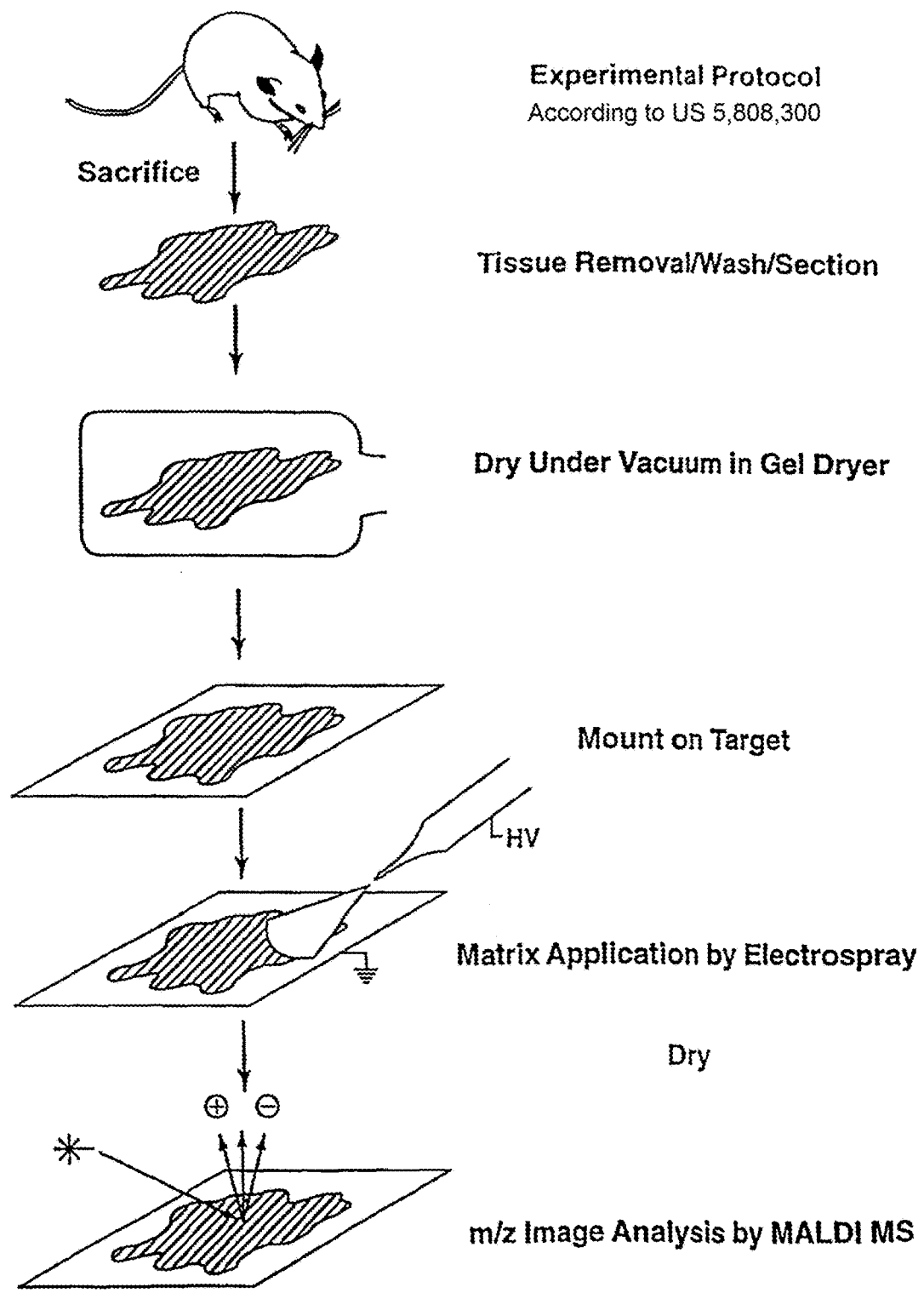
FIG. 1 depicts a workflow for mass spectrometric acquisitions from a tissue section, known from the prior art disclosure U.S. Pat. No. 5,808,300.
Figure 2:
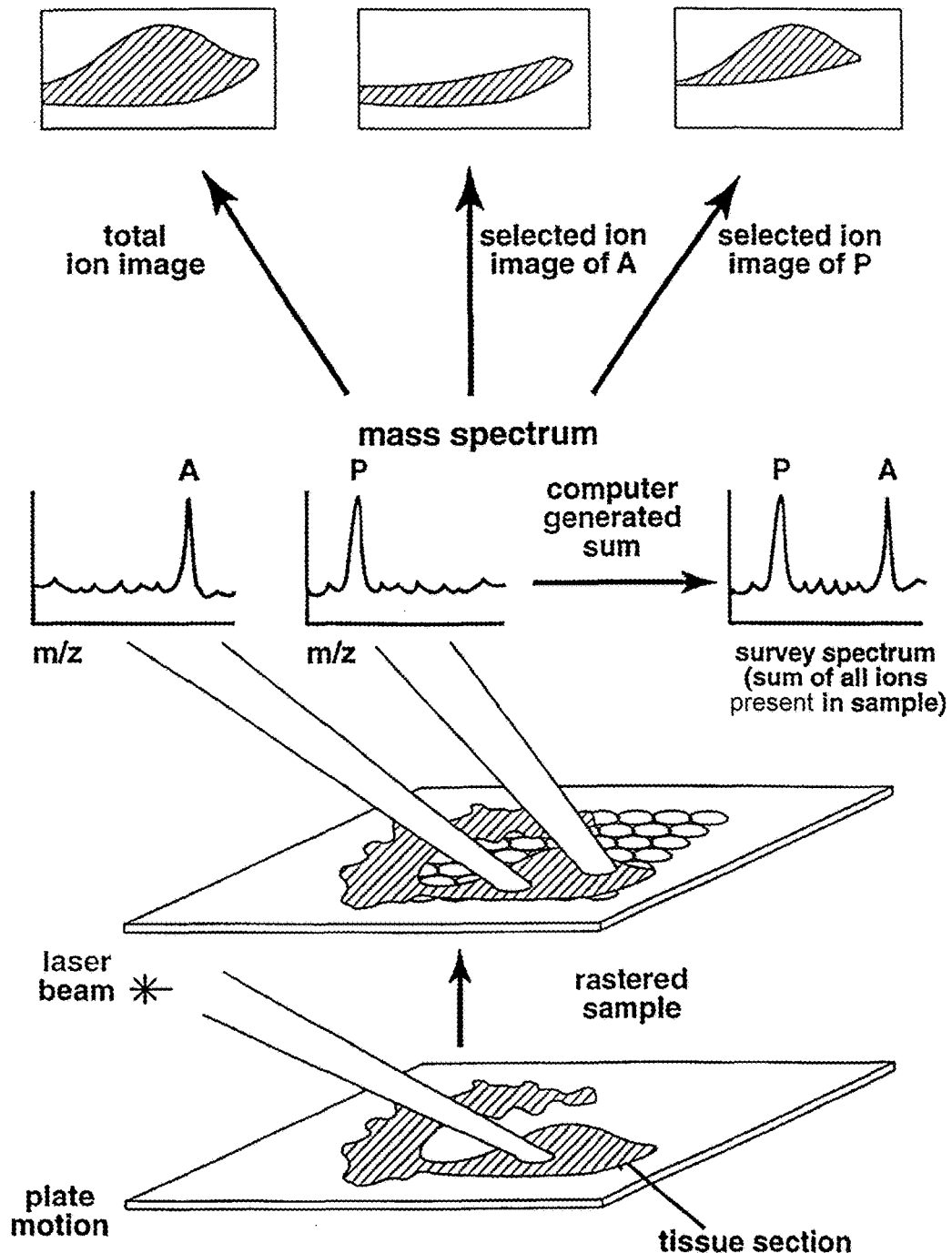
FIG. 2 presents an associated mass spectrometric imaging protocol for the tissue section, likewise known from the prior art disclosure U.S. Pat. No. 5,808,300.

While the invention has been shown and described with reference to a number of different embodiments thereof, it will be recognized by those skilled in the art that various changes in form and detail may be made herein without departing from the scope of the invention as defined by the appended claims.

MALDI imaging is a technique that promises great potential for the analysis of tissue sections. A large number of proof-of-concept studies have shown that it is possible to classify e.g. tumour types. The initial development of MALDI imaging was focused on frozen sections. In a clinical workflow, however, the use of fresh frozen tissue is the exception due to its quite limited availability while the norm is to analyse formalin-fixed, paraffin-embedded tissue. Therefore, large collections of formalin-fixed tissue with detailed patient history are available, often referred to as a "gold-mine" by those who seek to gain scientific insight therefrom.

However, for the preparation of MALDI imaging samples, those tissue sections usually require additional steps in the sample preparation. Currently, the most common approach to analyse FFPE tissue is to perform an antigen retrieval step followed by a spatially resolved enzymatic digest. All these steps introduce potential sources of variation and need to be optimized for an optimal result. One major problem for such optimization experiments is that no objective quality criteria exist to measure the key parameters in the resulting datasets, such as any analyte migration that would contribute to limiting the spatial resolution. Therefore, the development has relied hitherto on expert judgement, which is not satisfactory for a systematic improvement of sample preparation protocols. In the present disclosure, a workflow is proposed that allows the objective and semi-quantitative evaluation of the quality of a mass spectrometric imaging dataset.

Since there is a continuous need to obtain best spectral quality and the best possible spatial resolution where the requirement for the latter is determined in most cases by the biology, such as the typical dimension of anatomical features of interest, it is necessary to evaluate those two parameters independently from each other.

Measuring the spatial resolution is especially tricky when compared to optical imaging. In microscopy, for example, the spatial resolution is defined as the smallest distance at which two separate objects can still be seen as separate objects. In mass spectrometric imaging, it is quite common to use the grid point dimension or pixel size (usually an area scanned by the desorbing beam to render a sum mass spectrum) as a surrogate for spatial resolution, with the pixel size being defined as the physical limit of the instrument to measure two separate pixels. But this does not translate directly into a resolution in the sense of the optical imaging definition especially because the wet chemistry during the sample preparation and/or processing, such as an enzymatic digest or a matrix application step, often delocalizes the analytes in the tissue and thus blurs the mass spectrometric image beyond any purely instrumental limitations.

However, in optical imaging, the resolution can be easily measured by using artificial patterns like gratings with different line width and spacing. Also for mass spectrometric imaging, approaches using grating-like structures have been proposed but they cannot remedy the problem because tissue usually behaves quite differently upon wet treatment than any artificial or synthetic non-tissue sample [M. Passarelli et al.: Development of an Organic Lateral Resolution Test Device for Imaging Mass Spectrometry, Anal. Chem. 2014, 86, 9473-9480; and F. Zubair et al.: Standard Reticle Slide to Objectively Evaluate Spatial Resolution and Instrument Performance in Imaging Mass Spectrometry, Anal. Chem. 2016, 88, 7302-7311]. This latter argument also applies to an early study of Bernhard Spengler and co-workers where dyes have been used to visualize overlap regions in a laser desorption ionization mass spectrometry scan of an aluminium target painted with two different felt pens [B. Spengler et al.: Scanning Microprobe Matrix-Assisted Laser Desorption Ionization (SMALDI) Mass Spectrometry: Instrumentation for Sub-Micrometer Resolved LDI and MALDI Surface Analysis, J Am Soc Mass Spectrom 2002, 13, 735-748].

In a clinical workflow as well as for optimizing sample preparation conditions for mass spectrometric imaging, both the data from the tissue sample itself as well as the analytical workflow should be trustworthy. In order to ensure the latter, it is proposed to place a suitable control reference sample next to the real analytical tissue section(s) to be investigated on the same sample support and to process them alongside. This quality control reference sample comprising a least two distinguishable tissue types should be obtainable in comparatively high numbers at constant and reproducible quality.

Figure 3:
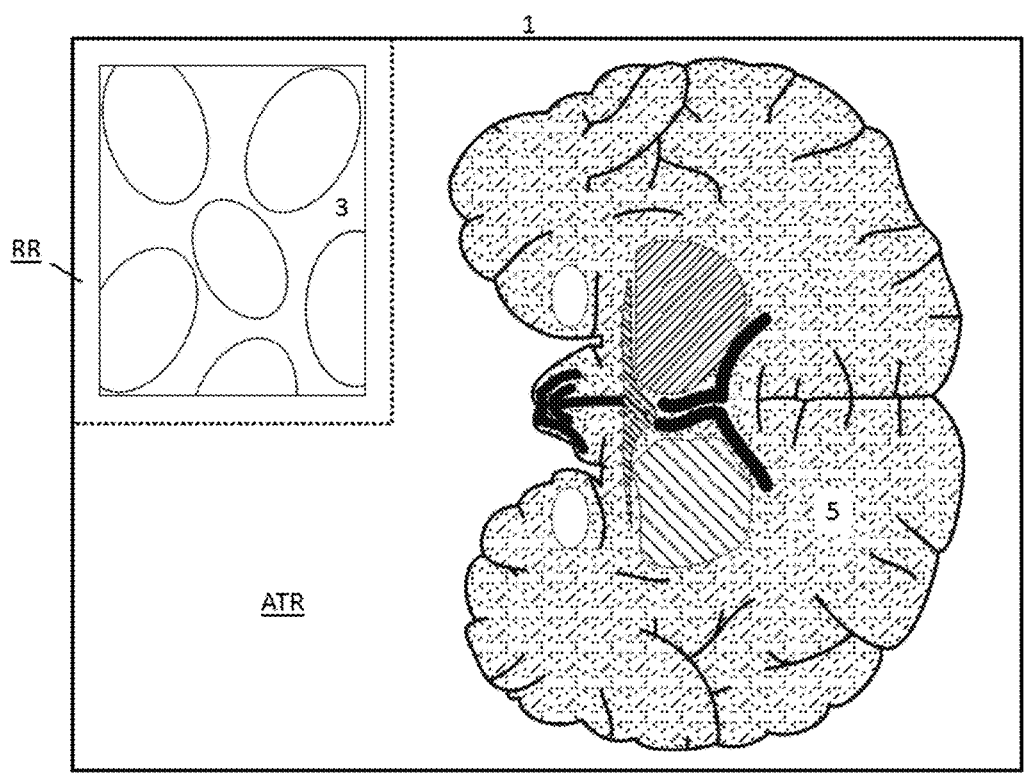
FIG. 3 presents an exemplary sample support ready to carry a reference sample and an analytical tissue section for mass spectrometric imaging.

FIG. 3 presents a sample support 1 suitable for mass spectrometric imaging in a front view. The sample support 1 can be a flat, conductive plate, such as a stainless steel plate, an ITO-coated glass plate or a ceramic plate correspondingly coated. The loadable surface of the sample support 1 is divided in this example into two separate regions RR and ATR. A first region RR is designated to carry a reference tissue sample 3, such as a mouse testis section. The second region ATR is designated to carry an analytical tissue section 5 (or more than one analytical tissue section) to be investigated, such as a brain section from an animal as depicted by way of example.

The general idea of the present invention is to place a reference sample 3 of known tissue configuration next to the analytical sample(s) 5 on the same sample support in order to jointly subject the two (or more) tissue samples 3, 5 to the same preparation and processing conditions. This action allows the determination of an analyte delocalization feature in the reference sample 3 of known anatomical structures and the subsequent tagging of the analytical sample(s) 5 and the mass spectrometric images generated therefrom with this delocalization feature for later evaluation and comparison with other imaging measurements, as the case may be.

The sample support 1 can be delivered from the manufacturer as a kit-of-parts with a reference sample 3 already being deposited in the reference sample region RR and thus ready for being prepared together with one or more analytical tissue samples 5 to be laid onto the sample support 1 in the customer's laboratory. In the alternative, FFPE blocks of suitable reference tissue from which the researcher can cut the required slices can also be provided separate from the sample support.

Figure 4:
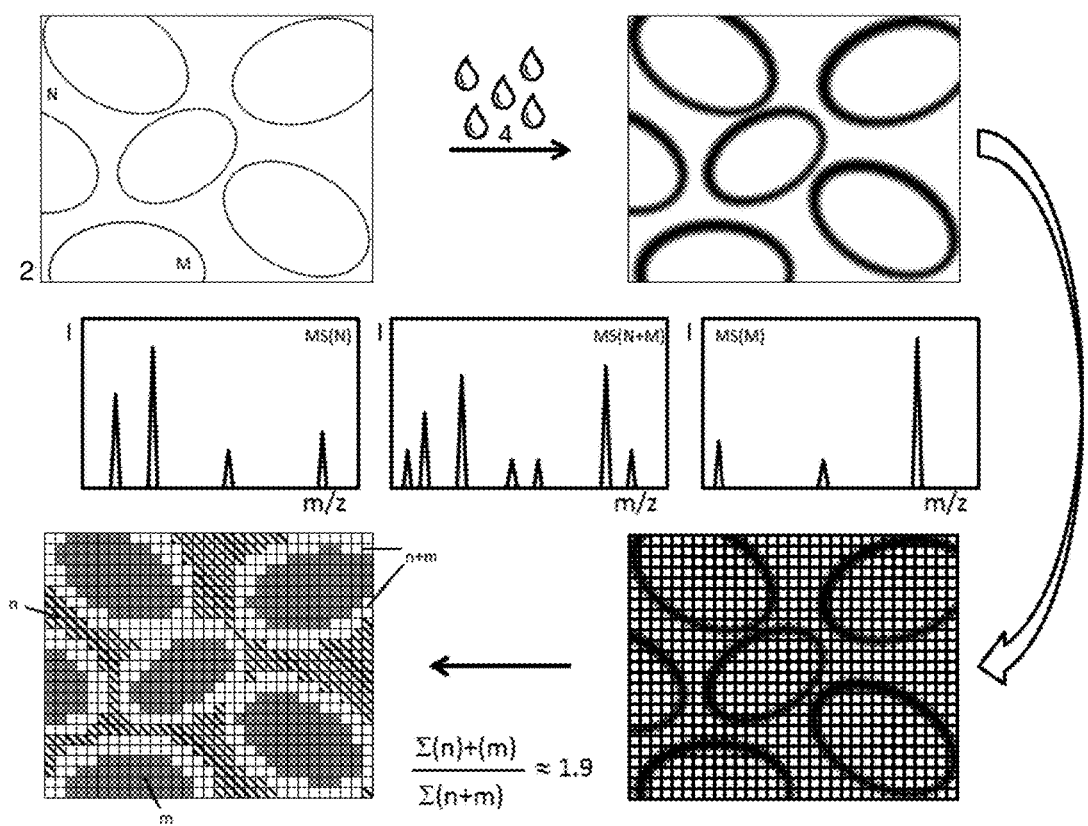
FIG. 4 illustrates the principles of the present disclosure exemplified using a mixed mass signal profile approach.

FIG. 4 shows a schematic of a first operating principle of a method according to the present disclosure. Starting point is a reference sample which takes the form of a tissue section 2 with two clearly delimited tissue types N, M. A first tissue type M manifests itself in cellular islands whereas the second type N comprises the interstitial space in between those cellular islands in this example, see top left of the illustration. A rat or mouse testis section could be taken as an example of such a tissue section 2 with the tubuli being the islands. As can be seen, the original, sharply delimited borderlines between the tissue types N, M of the tissue section 2 become blurred upon exposure to wet chemistry 4 in the course of sample preparation and processing for analysis, such as applying a liquid matrix substance for MALDI ionization or a liquid enzyme for an enzymatic digest (for example following antigen retrieval or decrosslinking). In other words, the analytes in the tissue become delocalized during such treatment, see top right of the illustration, where the degree of delocalization may depend on the parameters observed during the wet treatment. It goes without saying that such delocalization is highly unfavourable as it reduces the ability to precisely localize the occurrence of the analytes on any analytical tissue section to be investigated.

When the tissue section 2 is gradually scanned with a desorbing beam in order to generate spatially resolved mass spectra, these spatially resolved mass spectra in the tissue type regions that are sufficiently spaced apart from the respective other tissue type will still show the same "pure" analyte composition or mass signal profile that is characteristic of the particular underlying tissue type N, M, as illustrated with the leftmost and rightmost schematic mass spectra MS(N), MS(M) at the centre. It is to be noted that the difference in the mass signal profiles could be tied to the presence or absence of a single mass signal in the spectra MS(N), MS(M), such as exemplified in the prior art FIG. 1 for the molecules A and P, but in many cases it could manifest itself in a group of mass signals constituting a particular signature or profile as shown here. Peak picking algorithms, such as disclosed in U.S. Pat. No. 6,288,389 B1 the content of which is incorporated herein by reference in its entirety, can be used to identify these characteristic mass signal groups.

At the borderline between the different tissue types N, M, as visualized by the grid which is laid over the tissue section, see bottom right of the illustration, the effect of the delocalization is most pronounced since there the different mass signal profiles of the tissue types come to mix and thus overlap in adjacent grid points or pixels, as illustrated with the middle schematic mass spectrum MS(N+M) at the centre of the picture. In this illustration, one grid point could correspond to a pixel in the image either having the size of the desorbing beam or a pixel area scanned by the desorbing beam to render a sum mass spectrum. This size could typically be in the range of several micrometers, such as 1 to 50 micrometers or 10 to 100 micrometers, for example.

A very simple but likewise very effective way of deducing an analyte delocalization feature in the reference sample consists in counting the number of grid points or pixels n, m which can be classified as containing either one of the "pure", distinct mass signal profiles MS(N), MS(M) which are indicative of a particular tissue type N, M and those grid points or pixels n+m having combined or mixed mass signal profiles MS(N+M) which comprise components from several tissue types. This classification can be visualized for human inspection by showing a corresponding colour coded image of the desorption grid pattern or raster, such as red for the first "pure" tissue type N, green for the second "pure" tissue type M, and yellow for the mixture N+M (RGB colour scheme).

In order to find the mixed grid points or pixels, the complete images for the two particular mass signal profiles MS(N), MS(M) can be statistically evaluated. Intensities of both mass signal profiles over the entire images may be scaled linearly and stored in individual channels for each pixel. These channels of pure mass signal content can be designated with the colours red and green (RGB scheme). An alternative could comprise using the La*b* scheme as it is better adapted to human perception. The zero intensity can be set to the third percentile of the respective intensity values, and the maximum intensity to the 97th percentile. Intensity values below the third or above the 97th percentile may be set to zero or full intensity, respectively. Out of the "red" and the "green" channels for each pixel of the image, a virtual "yellow" channel can be calculated. The intensity of the "yellow" channel for each pixel may be calculated as the minimum of that in the "red" and the "green" channel for this pixel, for instance.

Then the image to be shown to a user can be spatially segmented: If the intensity of the virtual "yellow" channel of a pixel is above a threshold multiplied by the intensity of the maximum of the red or green channel in that pixel, it can be displayed as a mixed ("yellow") pixel. Otherwise the pixel can be displayed as red if the red channel is more intense than the green pixel, or as a green pixel otherwise.

Forming a ratio between the two "pure" and "mixed" grid point numbers Σ(n)+(m)/Σ(n+m) as a "quality score" allows determining the degree of delocalization that happened in the tissue section 2 under investigation as reference sample. In the present example shown, the number of mixed pixels results as 267 whereas the number of pure pixels amounts to 508 (on an exemplary grid of 25 by 31 pixels). Thus, the above ratio is about 1.9. It goes without saying that meaningful information can be obtained only when the delocalization dimension exceeds the instrumentally-defined minimum, normally the pixel size or grid point dimension which, in turn, finds its lower limit in the dimension or size of the desorbing beam. Thus, the smaller the pixels are, the easier it is to detect analyte redistribution. Storing this above calculated ratio together with the mass spectrometric images taken concurrently from the actual analytical tissue section (s) prepared on the same sample support together with the mode of how this quality score was deduced facilitates later comparison with tissue section analyses that took place at different times and/or in different places but using the same sample preparation/processing conditions and/or measurement conditions, as the case may be.

Figure 5:
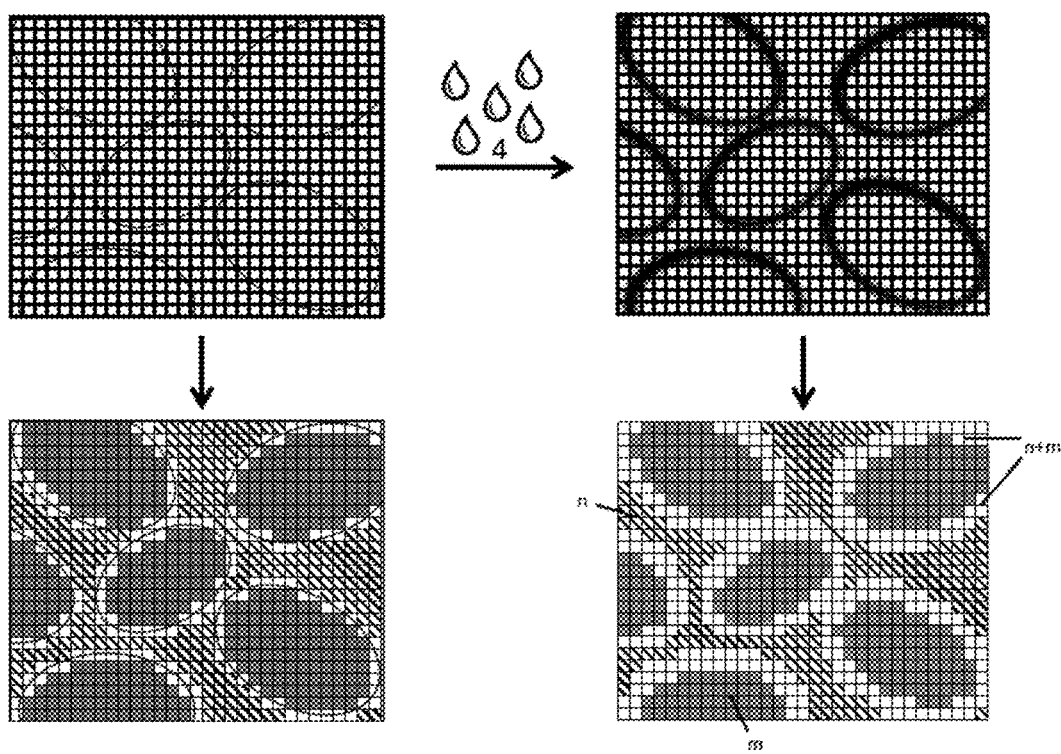
FIG. 5 shows a variant of the example from FIG. 4, including an optical image of the still untreated reference sample.

A variant of the above described method, schematically illustrated in FIG. 5, includes the acquisition of an optical image of the tissue section reference sample before liquid treatment 4 during a preparation or processing step. Thus, the optical image can retain a very high spatial resolution and show comparatively narrow, sharply defined boundaries between different tissue types which match the boundaries between the underlying specific mass signal profiles quite well. If now this high resolution optical image is overlaid with the pixel grid to be used to scan the tissue section mass spectrometrically with the desorbing beam, see top left of the figure, the number of those pixels or grid points clearly intersected by the boundary lines can be identified in the optical image by the conspicuous, comparatively sharp border contours between the tissue type areas N and M, see bottom left of the figure (borderlines shown for the sake of clarity). This number should equal the number of pixels in the overlap areas, as defined for the previous embodiment, if there is no detectable analyte delocalization, which means no analyte delocalization exceeding the average pixel size since this instrumentally poses the minimum mass spectrometric spatial resolution to be obtained in any case. Obviously, the expected number of mixed pixels or grid points cannot be smaller than that because, even when no blurring takes place in the tissue, these intersected pixels or grid points will always contain mass signal profiles from both sides of the tissue type boundaries thereby unavoidably giving spatially resolved mass spectra of mixed mass signal content.

If now analyte delocalization takes place beyond the average pixel size during preparation and processing, a number of pixels or grid points adjacent to the intersected pixels or grid points will see an influx of molecules from the adjacent tissue areas, which becomes detectable by the particular mass signal profiles in the mass spectra. The borderlines between the different tissue types become blurred, see top right of the figure, so that potentially a larger number than just the expected minimum pixel number inferred from the untreated reference sample will be affected by analyte migration during the wet chemistry step. The number of overlap pixels can be determined from the mass spectrometric image of the reference sample, see bottom right of the figure, and compared to the expected number calculated under the assumption of no additional analyte redistribution. The deviation between the expected minimum number of mixed pixels, see bottom left in the figure, from the one actually measured mass spectrometrically, see bottom right in the figure, yields a good standard to evaluate the degree of underlying delocalization processes. In the example shown, the minimum number results as 159 whereas the one actually measured is 267, making for an increase of about two thirds. This deviation can serve as the quality score with which the actual analytical tissue sections measured concurrently and their images can be tagged.

In a particular variant of this afore-described method, the raster with which the reference sample is scanned can be laid out such that no intersected pixels occur before liquid exposure; in other words, the pixel pattern is set such that the borderlines between different tissue types smoothly align with the outer pixel limits but do not cross them (while the pixel raster for the analytical tissue section can remain regular). This can be ascertained from the untreated sample with the aid of an optical image, for instance. In so doing, the expected minimum number of intersected or mixed cell type pixels may be set to zero by virtue of the adapted, irregular pixel arrangement thereby greatly simplifying the assessment.

Figure 6A:
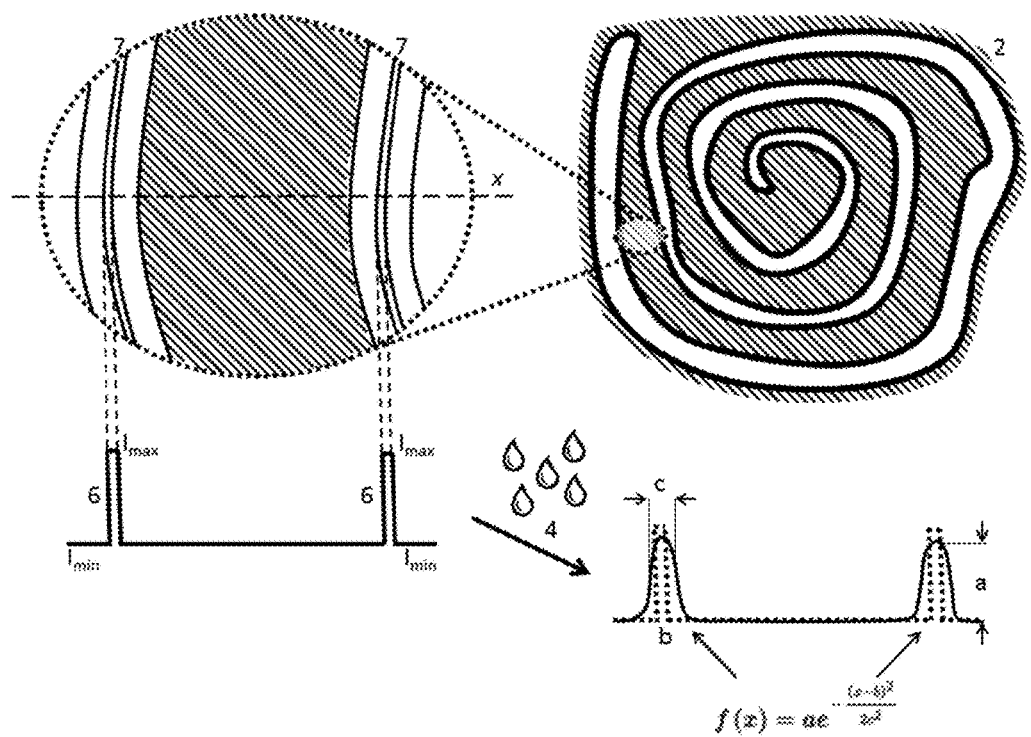
FIG. 6A is the first of two figures illustrating the principles of the present disclosure exemplified using a line-width approach.

FIG. 6A illustrates a schematic of a second operating principle of a method according to the present disclosure. Starting point is a reference sample which takes the form of a colon coil section 2 in this example, with tissue between the coil windings shown as hatched areas and the colon walls shown as bold lines, see top right of the figure. The colon coil can be taken from rodents, such as mice and rats, for instance. The colon wall comprises several layers of distinct tissue types wherein a middle muscular layer 7 depicted in this example is the thinnest at a width of about 150 micrometers, see top left of the figure. This middle layer 7 has a characteristic mass signal profile by which it can easily be discriminated from the adjacent tissue layers. Consequently, this middle layer 7 is well suited to investigate the degree of analyte migration in the tissue under exposure to liquids and wet chemistry 4.

FIG. 6A depicts also a horizontal trace (dashed line x) which represents a path a desorbing beam, such as a MALDI laser beam, could follow when scanning the reference tissue sample 2. In so doing, the desorbing beam would pass over the alternating tissue types in the interstitial regions as well as the different wall layers, thereby producing a grid or raster of spatially resolved mass spectra which contain distinguishable mass signal profiles for each tissue type as has been exemplified before in the context of previous examples (see MS(N) and MS(M) in FIG. 4, for instance).

The result of such scanning can be illustrated as an intensity diagram wherein the strength or amplitude of the particular mass signal profile ($I_{min}$ to $I_{max}$) is plotted over pixel or grid point position x, see bottom left of the figure. In the unblurred or non-delocalized case, for instance before any wet chemistry treatment 4, which can be inferred from an optical image, at the borderline between two tissue types, such as the middle muscular layer 7 and the adjacent layers, there is shown a sharp intensity transition 6 to occur including a steep rise of the particular mass signal profile characteristic of the middle muscular layer 7. In an optical image of sufficiently high resolution, the different tissue regions could be discernible and delimitable from one another by colour and/or brightness contrast of the individual layers, for instance.

The situation changes when the colon coil section 2 has been exposed to wet chemistry 4 during sample preparation and/or processing, such as the application of a liquid matrix substance for MALDI ionization or a liquid enzyme for protein digestion. This transition is schematically depicted at the bottom right of the figure. The liquid penetrates into the tissue layers and takes its effect there. Unfortunately, this penetration cannot normally be controlled in the sense that the liquid would just proceed into the depth of the tissue but it will also spread laterally, thereby forming some kind of liquid connection between adjacent tissue regions that are normally separate so that a certain lateral exchange of analytes can occur there-between in the wet condition.

Such delocalization takes the most pronounced form in small anatomical structures, such as the thin middle muscular layer 7 of the colon wall. Instead of a sharp distinction between the particular mass signal profiles of adjacent tissue types, intermediate transition areas show up. This deterioration of mass spectrometric spatial resolution through analyte delocalization, which may not be so conspicuous in an optical image of the wet chemistry-treated reference sample, if discernible at all, can be described mathematically at least semi-quantitatively by a convolution of an initially highly resolved structure with an operator that can take the form of a function f(x) which is representative of the blurring that happens during the wet chemistry stages 4 of sample preparation and processing.

The spreading of any particular mass signal profile can be quantified by fitting an analytical curve to the spatial intensity profile where care should be taken in the present example that the trace of the desorbing beam x is aligned as perpendicular to the extension of the colon wall as possible. However, when rastering a colon coil section 2 that comprises a plurality of windings, it should always be possible to find traces having such perpendicular alignment (even with a regular pixel raster). The analytical curve can be a Gaussian bell curve as this describes the diffusion processes occurring during analyte migration quite well. A possible parametrization would be $$f(x) = a \cdot e^{-\frac{(x-b)^2}{2c^2}}$$

where a is the maximum amplitude of the signal, x the direction of the desorbing beam trace, b the centre position and c the width parameter (standard deviation) of the bell curve. The width parameter c can be easily reckoned into a full width at half maximum (FWHM) or any other suitable width measure and represents a good proxy for the gradient of the rise of the curve. The larger it gets, the further the analytes have migrated and the more the mass spectrometric image is blurred.

Figure 6B:
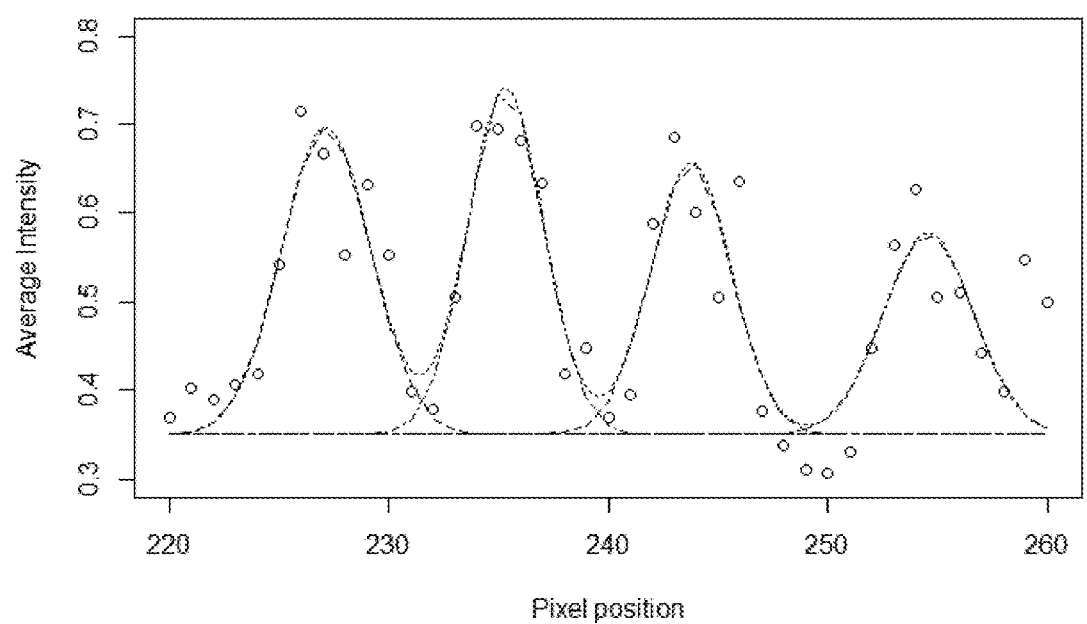
FIG. 6B is the second of two figures illustrating the principles of the present disclosure exemplified using a line-width approach.

FIG. 6B shows the result of fitting Gaussian bell curves to data from an actual imaging measurement of a rat colon coil section that was provided as an FFPE sample, treated with a tryptic digest after deparaffinization and antigen retrieval as well as prepared with a liquid matrix substance for MALDI MS imaging using a pixel size of 50 micrometers square length. Such reference sample shows the double effect of two liquid treatments during preparation. The mass signal profile tracked the mass peak at m/z 1095 characteristic for a middle muscular layer in the colon wall. An intensity baseline was considered. A good guess of the initial parameters of the Gaussian bell curve has proven to be helpful for this approach, in particular for the centre position b of the Gaussians. The full width at half maximum of the four Gaussians in FIG. 6B quite consistently results in 243, 208, 221, and 246 (all in micrometers from left to right).

When accounting for the fact that the middle muscular layer in the colon wall is not a true "line"-type source of the mass signal and that the width of the selected anatomical structure is in the order of 150 micrometers, upon simple subtraction which renders a reasonable approximation, a delocalization width parameter of between 50 and 100 micrometers remains. If it is assumed that two structures can be seen as different if the intensity between them drops to about 50%, then this resolution is in line with the Nyquist-Shannon theorem. This theorem states that with the pixel size of 50 micrometers used, two objects can only be seen as different objects if their distance is larger than twice the pixel size.

The approach described in conjunction with FIGS. 6A and 6B allows tagging the analytical tissue samples processed and measured alongside the reference sample having a sufficiently thin, line-like (anatomical) structure with a semi-quantitative analyte delocalization feature as it takes the form of an actual length parameter.

It may prove helpful for some analyses to use a spatial mask in order to exclude grid points or pixels that are not measured on tissue and would therefore not contain any mass spectrometric information of interest. In this case, a co-registered primary optical image of the untreated tissue can be transferred into a black and white mask by thresholding. For each grid point or pixel, it can be checked if it was measured above a white pixel (background) or a black pixel (tissue) of that mask. Non-tissue pixels may be disregarded in the evaluation.

Figure 7:
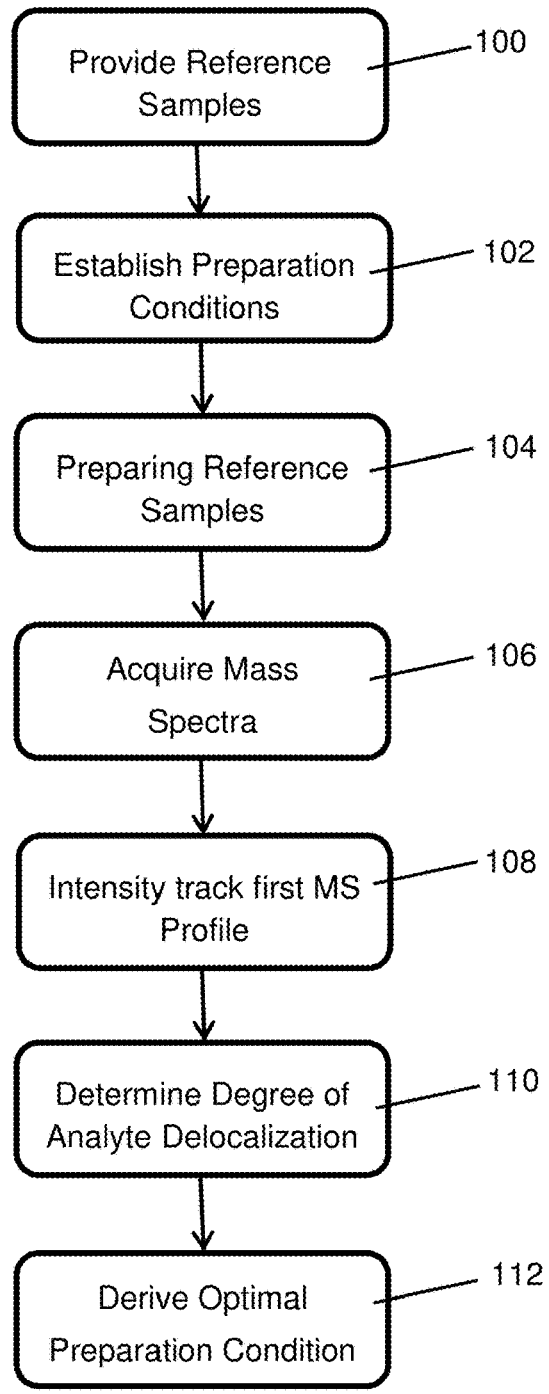
FIG. 7 shows a flow diagram for an optimization procedure according to principles of the present disclosure.

FIG. 7 shows a flow diagram of an exemplary method for optimizing sample preparation conditions for mass spectrometric imaging of a tissue section. Step 100 includes providing a plurality of like reference samples, the reference samples comprising tissue which has adjacent regions of a first type and a second type of biological material, the first type of biological material being characterized by a first mass signal profile. Step 102 includes establishing a plurality of different preparation conditions for the plurality of reference samples, which conditions comprise exposure of a reference sample to wet chemistry. Step 104 includes preparing each of the plurality of reference samples for analysis in accordance with one set of preparation conditions from the plurality of different preparation conditions. Step 106 includes acquiring spatially resolved mass spectra from the plurality of reference samples. Step 108 includes intensity-tracking the first mass signal profile over the spatially resolved mass spectra of each of the plurality of reference samples. Step 110 includes deducing a degree of analyte delocalization in each of the plurality of reference samples from the intensity tracks. Step 112 includes deriving an optimal preparation condition from the plurality of different preparation conditions as that which causes least delocalization in the plurality of reference samples.

The above description has focused on MALDI mass spectrometric imaging of FFPE tissue sections. Those of skill in the art will understand, however, that the principles of the present disclosure can be equally applied to other sample types, such as frozen tissue sections, and other ionization techniques, such as DESI and SIMS.

Further, the mixed pixel approach has been described above with respect to a testis sections and the line-width approach with respect to a colon coil section. It goes without saying, however, that the mixed pixel approach could likewise be applied to a colon coil section to probe the interfaces between the individual layers in the colon wall, or that the line width approach could be applied to a testis section by intensity-tracking a basal lamina layer therein, for instance.

Generally, the invention has been shown and described above with reference to a number of different embodiments thereof. It will be understood, however, by a person skilled in the art that various aspects or details of the invention may be changed, or various aspects or details of different embodiments may be arbitrarily combined, if practicable, without departing from the scope of the invention. Generally, the foregoing description is for the purpose of illustration only, and not for the purpose of limiting the invention which is defined solely by the appended claims, including any equivalent implementations, as the case may be.

The invention claimed is:

1. A method for evaluating a quality of preparations of an analytical tissue section for mass spectrometric imaging, comprising:
    providing a sample support suitable for mass spectrometric imaging;
    depositing the analytical tissue section and a reference sample on the sample support, wherein the reference sample comprises tissue which has adjacent regions of a first type and a second type of biological material, the first type of biological material being characterized by a first mass signal profile;
    jointly preparing the analytical tissue section and the reference sample for analysis, which includes exposure of the analytical tissue section and the reference sample to wet chemistry;
    acquiring spatially resolved mass spectra from the analytical tissue section and the reference sample in a same measurement run;
    intensity-tracking the first mass signal profile over the spatially resolved mass spectra from the reference sample;
    deducing an analyte delocalization feature from the intensity track(s); and
    tagging a mass spectrometric image produced from the spatially resolved mass spectra of the analytical tissue section using the analyte delocalization feature.

2. The method of claim 1, further comprising using at least one of a colon coil section, testis section, spleen section, skin section, blood vessel, spine section and sections from a tissue surrogate comprising layers of cultured cells as the reference sample.

3. The method of claim 1, further comprising intensity-tracking a second mass signal profile characteristic for the second type of biological material over the spatially resolved mass spectra, and, using the different intensity tracks, finding acquisitions among the spatially resolved mass spectra from the reference sample that belong to either the first type or the second type of biological material by their first and second mass signal profiles, respectively, to define corresponding distinct areas on the reference sample, and finding those acquisitions which are characterized by a mixture of the first and second mass signal profiles to define overlap areas on the reference sample.

4. The method of claim 3, wherein the deducing comprises counting the number of mass spectra in the distinct areas and that in the overlap areas and forming a ratio thereof as the analyte delocalization feature.

5. The method of claim 1, wherein the intensity track(s) of the first mass signal profile crosses a thin and elongate structure in the reference sample, and deducing the analyte delocalization feature comprises using a fitting algorithm.

6. The method of claim 5, wherein the fitting algorithm employs an analytical curve and accounts for a finite width of the thin and elongate structure.

7. The method of claim 6, wherein the analytical curve is a Gaussian bell curve.

8. The method of claim 5, wherein the thin and elongate structure comprises one of a muscular layer and a basal lamina layer.

9. The method of claim 1, further comprising masking-out non-tissue acquisitions of the spatially resolved mass spectra from the intensity-tracking and deducing steps.

10. The method of claim 9, wherein the non-tissue acquisitions for the masking-out are identified by using an optical image of the reference sample and matching it to the spatially resolved mass spectra from the reference sample.

11. The method of claim 1, further comprising using chemically fixed samples embedded in an organic solid material as the analytical tissue section and the reference sample.

12. The method of claim 11, wherein FFPE samples are used as the analytical tissue section and the reference sample.

13. The method of claim 11, wherein jointly preparing the analytical tissue section and the reference sample for analysis includes subjecting the chemically fixed samples embedded in an organic solid material to antigen retrieval in order to facilitate decrosslinking therein.

14. The method of claim 1, wherein jointly preparing the analytical tissue section and the reference sample for analysis includes subjecting them to an enzymatic digest which substantially preserves spatial distribution.

15. The method of claim 14, wherein the enzymatic digest is a tryptic digest or glycan digest.

16. The method of claim 1, wherein jointly preparing the analytical tissue section and the reference sample for analysis includes applying a layer of matrix substance for matrix-assisted laser desorption/ionization (MALDI) onto the analytical tissue section and the reference sample.

17. The method of claim 1, further comprising establishing and expanding a database that contains a plurality of images from investigated analytical tissue sections and the associated analyte delocalization features in order to facilitate comparison between the latter.

18. The method of claim 1, wherein two or more analytical tissue sections are deposited next to the reference sample on the same sample support.

19. A kit-of-parts for a mass spectrometric imaging experiment, comprising a mass spectrometric sample support having a surface which is divided into a first area assigned to receiving a reference sample and a second area assigned to receiving an analytical tissue section, wherein the first area carries a reference tissue which has adjacent regions of a first type and a second type of biological material, the first type of biological material being characterized by a first mass signal profile and the second type of biological material being characterized by a second mass signal profile which is not identical to the first mass signal profile, and wherein the first and second mass signal profiles are configured such as to allow deducing a degree of spatial migration from at least one of the first type of biological material to the second type of biological material and vice versa during preparation of the reference sample for the mass spectrometric imaging experiment.

20. A method for optimizing sample preparation conditions for mass spectrometric imaging of a tissue section, comprising:

providing a plurality of like reference samples, the reference samples comprising tissue which has adjacent regions of a first type and a second type of biological material, the first type of biological material being characterized by a first mass signal profile;

establishing a plurality of different preparation conditions for the plurality of reference samples, which conditions include exposure of a reference sample to wet chemistry;

preparing each of the plurality of reference samples for analysis in accordance with one set of preparation conditions from the plurality of different preparation conditions;

acquiring spatially resolved mass spectra from the plurality of reference samples;

intensity-tracking the first mass signal profile over the spatially resolved mass spectra of each of the plurality of reference samples;

deducing a degree of analyte delocalization in each of the plurality of reference samples from the intensity tracks; and deriving an optimal preparation condition from the plurality of different preparation conditions as that which causes least delocalization in the plurality of reference samples.

* * * * *